United States Patent [19]

Matsumoto

[11] Patent Number: 5,615,278
[45] Date of Patent: Mar. 25, 1997

[54] METHOD AND APPARATUS FOR IMAGE PROCESSING BY CORRECTING THE POSITION OF EACH PART OF AN EYE FUNDUS IMAGE PRODUCED BY AN OPTICAL IMAGING SYSTEM

[75] Inventor: Kazuhiro Matsumoto, Tokyo, Japan

[73] Assignee: Canon Kabushiki Kaisha, Tokyo, Japan

[21] Appl. No.: 372,836

[22] Filed: Jan. 13, 1995

Related U.S. Application Data

[63] Continuation of Ser. No. 57,454, May 7, 1993, abandoned, which is a continuation of Ser. No. 798,050, Nov. 27, 1991, abandoned, which is a continuation of Ser. No. 564,170, Aug. 8, 1990, abandoned.

[30] Foreign Application Priority Data

Aug. 24, 1989 [JP] Japan ................................ 1-220057

[51] Int. Cl.⁶ ............................... A61B 3/14; G06T 5/00
[52] U.S. Cl. .......................... 382/128; 382/254; 348/78
[58] Field of Search ........................... 382/115, 117, 382/128, 274; 351/206, 211; 348/335, 345, 78

[56] References Cited

U.S. PATENT DOCUMENTS

| | | | |
|---|---|---|---|
| 3,879,113 | 4/1975 | Howland et al. | 351/206 |
| 4,019,813 | 4/1977 | Cornsweet et al. | 351/211 |
| 4,251,800 | 2/1981 | Sanner et al. | 382/54 |
| 4,266,862 | 5/1981 | Trötscher et al. | 351/14 |
| 4,298,944 | 11/1981 | Stoub et al. | 382/6 |
| 4,606,626 | 8/1986 | Shinohara | 351/169 |
| 4,679,919 | 7/1987 | Itoh et al. | 351/206 |
| 4,820,037 | 4/1989 | Kohayakawa et al. | 351/211 |
| 4,828,381 | 5/1989 | Shindo | 351/206 |
| 4,848,896 | 7/1989 | Matsumoto | 351/211 |
| 4,906,078 | 3/1990 | Inabata et al. | 350/423 |
| 4,952,049 | 8/1990 | Matsumoto | 351/211 |
| 4,992,859 | 2/1991 | Yoshida | 358/227 |

OTHER PUBLICATIONS

Rowe et al. "A charge coupled device imaging system for ophthamology" SPIE Proceedings V. 454 pp. 65–71, 1984.

*Primary Examiner*—Michael T. Razavi
*Assistant Examiner*—Larry J. Prikockis
*Attorney, Agent, or Firm*—Fitzpatrick, Cella, Harper & Scinto

[57] ABSTRACT

An image processing method and apparatus which obtains an image of an object to be inspected by an imaging optical system, and corrects the position of each part of the image. The position of the image depends on the relative disposition of the imaging optical system with respect to the object to be inspected at the time of obtaining the image to be inspected. By this arrangement, correct imaging of an eye fundus image can be performed regardless of imaging conditions which arise due to the difference in the distortion characteristics of the eye and an imaging optical system which images persons having far-sightedness and near-sightedness.

9 Claims, 4 Drawing Sheets

METHOD AND APPARATUS FOR IMAGE PROCESSING BY CORRECTING THE POSITION OF EACH PART OF AN EYE FUNDUS IMAGE PRODUCED BY AN OPTICAL IMAGING SYSTEM

This application is a continuation of application Ser. No. 08/057,454 filed May 7, 1993, now abandoned, which is a continuation of application Ser. No. 07/798,050 filed Nov. 27, 1991, now abandoned, which is a continuation of application Ser. No. 07/564,170, filed Aug. 8, 1990, now abandoned.

CROSS REFERENCE TO RELATED APPLICATION

Application Ser. No. 360,135 now U.S. Pat. No. 5,037,194 to Yoshimi Kohayakawa, Kenichi Kashiwagi, and Isao Matsumura was filed on May 31, 1989 and has the same Assignee as the present case.

BACKGROUND OF THE INVENTION

1. Field of the Invention

This invention relates to a method and an apparatus for image processing, which are adapted to correct an image such as, for example, an eye fundus image, and others, obtained by an imaging optical system, on the basis of its imaging conditions.

2. Related Background Art

The method of correcting an image such as an eye fundus image, etc. by an image processing apparatus is already known from, for example, U.S. Pat. No. 5,037,194. This known technique is of such a construction that any distortion in the image as taken may be corrected on the basis of the inherent image pickup distortion characteristics which the imaging optical system possesses. The image correction function f(r) provided for the imaging optical system, the sight of which has been adjusted in correspondence to an eye to be inspected of zero diopter, can be given as follows:

$$f(r) = 1.02371r - 0.01446r^2 + 0.00232r^3$$

This image correction function, however, is not at all different, even when the sight is adjusted in correspondence to the eye to be inspected of +10 diopters and or −10 diopters, hence there is no assurance that the image correction can always be done accurately. In other words, the distortion characteristics of the imaging optical system differs for a person to be inspected who is far-sighted and for a person to be inspected who is near-sighted, on account of which there is no assurance such accurate image correction can always be done.

SUMMARY OF THE INVENTION

In view of the inherent disadvantage with the conventional method and apparatus for image processing, it is the primary object of the present invention to provide an improved method and apparatus for image processing, which are capable of constantly performing accurate correction of images irrespective of the imaging conditions.

It is the secondary object of the present invention to provide an improved method and apparatus for processing an image of the eye fundus, which are capable of constantly performing accurate correction of the eye fundus image irrespective of the relative disposition of the imaging optical system with respect to an eye to be inspected, or the relative disposition of a fixed viewing optical system with respect to the imaging optical system.

According to one aspect the present invention relates to an image processing method, which comprises the steps of: obtaining an image to be inspected by and through an imaging optical system; and, at the time of obtaining the image to be inspected, correcting an image, which differs depending on imaging conditions concerning relative disposition of the imaging optical system with respect to an object to be inspected.

According to another aspect the present invention relates to an image processing method, which comprises the steps of: obtaining an image of the eye fundus to be inspected by and through an imaging optical system; and, at the time of obtaining the image of the eye fundus to be inspected, correcting an image which differs, depending on the imaging conditions concerning relative disposition of a fixed viewing optical system with respect to the imaging optical system.

According to still another aspect the present invention relates to an image processing apparatus, which comprises: input means for introducing an image to be inspected by and through an imaging optical system; input means for introducing, at the time of obtaining the image to be inspected, imaging conditions concerning relative disposition of the imaging optical system with respect to an object to be inspected; and means for correcting an image which differs, depending on the imaging conditions.

According to another aspect the present invention relates to an image processing apparatus, which comprises: input means for introducing an image of the eye fundus to be inspected by and through an imaging optical system; input means for introducing, at the time of obtaining the image of the eye fundus to be inspected, imaging conditions concerning the relative disposition of a fixed viewing optical system with respect to the imaging optical system; and means for correcting an image which differs, depending on the imaging conditions.

The foregoing objects, other objects as well as the specific construction and functions of the method and the apparatus for the image processing according to the present invention will become more apparent and understandable from the following detailed description thereof, when read in conjunction with the accompanying drawing.

DESCRIPTION OF THE PREFERRED EMBODIMENTS

In the following, the present invention will be explained in detail in reference to the accompanying drawings, showing the preferred embodiments as applied to the image processing apparatus for an eye fundus image.

Figure 1:
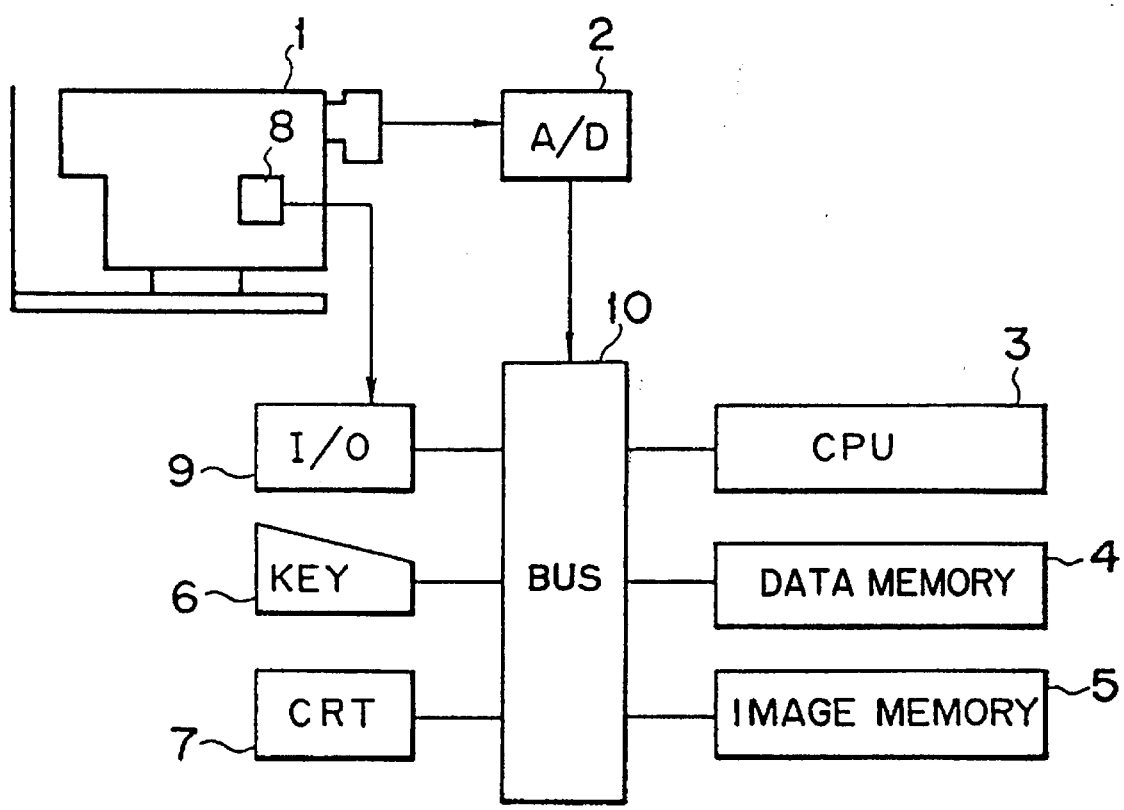
FIG. 1 is a block diagram showing a construction of the image processing apparatus according to one embodiment of the present invention.

Referring first to FIG. 1, showing the construction of the image processing apparatus according to one embodiment of the present invention, a reference numeral 1 designates an eye fundus camera, the imaging optical system of which has a focus adjusting means for adjusting the focus in accordance with the sight of an eye to be inspected; a reference numeral 2 designates an A/D converter for converting the eye fundus image data as taken by the eye fundus camera 1 into digital signals; a numeral 3 refers to data processing means such as a micro-computer, etc.; a numeral 4 refers to a data memory, in which are stored the processing sequences corresponding to the sight conditions of the eye fundus camera which has done its imaging operation; a reference numeral 5 represents an image memory to store therein the image data which have been converted into the digital signals; a reference numeral 6 denotes a keyboard; a numeral 7 refers to a monitoring television which displays the image data, etc. on the screen; a reference numeral 8 designates a detector which detects a rotational angle of a focus adjusting of the eye fundus camera, when it has been focus-adjusted, and forwards the angular information (i.e., viewing information for the image pickup) to an I/O interface 9. The I/O interface 9 converts the input information into a digital signal and sends it out to a bus bar 10.

The data processing means 3 once stores the above-mentioned image data on the bus bar 10 in the image memory 5.

The image taken by the fundus camera 1 has a concentric distortion (distortional aberration) with the optical axis as the center. Since the optical axis invariably constitutes the center of the image, this distortional aberration can be corrected in accordance with a function of r'=F(r) [where r denotes a distance of each image data from the center of image; r' represents a distance from the center of image in the image data as corrected; and F is a correction function to convert r into r'].

The function F can be represented, for instance, as follows:

$$F(r)=A(d)+B(d)r+C(d)r^2+D(d)r^3$$

[where: A(d), B(d), C(d) and D(d) are respectively the coefficients of the function F(r), which represent the rotational angles of the focus adjusting knob of the eye fundus camera when it is focus-adjusted; in other words, it is a function of the imaging sight d (diopter), which can also be represented as r'=F(r, d)].

More concretely, the image correction function F(r) provided for the imaging optical system, the sight of which has been adjusted in correspondence to an eye to be inspected of zero diopter, can be represented as follows:

$$F(r)=1.02371r-0.01446r^2+0.00232r^3.$$

On the other hand, the image correction function F(r) provided for the imaging optical system, the sight of which has been adjusted in correspondence to an eye to be inspected of +10 diopters, can be represented as follows:

$$F(r)=1.03885r-0.02394r^2+0.00377r^3.$$

Further, the image correction function F(r) provided for the imaging optical system, the sight of which has been adjusted in correspondence to an eye to be inspected of −10 diopters, can be represented as follows:

$$F(r)=1.010872-0.00658r^2+0.00108r^3.$$

In this way, the data processing means 3 detects the abovementioned imaging sight d on the bus bar 10, the detected value of which is substituted for the coefficients A(d), B(d), C(d) and D(d) of the function F in the data memory, thereby formulating the function F(r).

Figure 2:
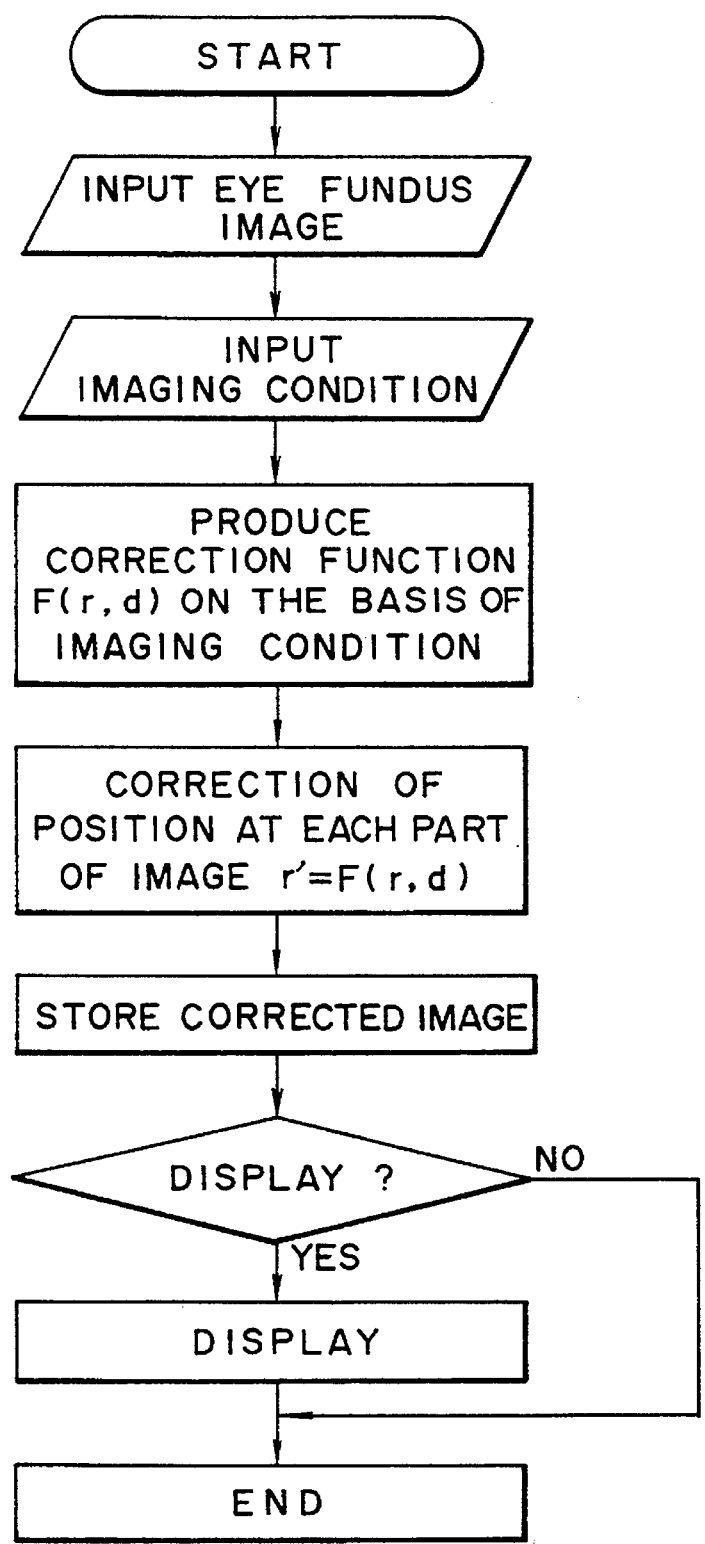
FIG. 2 is a flow chart for carrying out correction of the position of each and every part of an image.

By conversion of the image data by this data processing means 3 using this function F(r), the image data is corrected to be free from distortion; in other words, the position of each part of the image is rectified. The image data as corrected is again stored in the image memory 5, and displayed on the monitoring television upon instruction from the keyboard 6. A flow of a series of these processes is shown by a flow chart of FIG. 2.

In the above-described embodiment, an image output from the eye fundus camera and information representing a state of the imaging optical system have been introduced directly, as inputs, into the image processing means for the necessary processing. It is, of course, feasible that the eye fundus image recorded on photographic film, etc. by means of a general eye fundus camera is read by an image reading means, and the information as read out may be introduced as an input into the image processing means along with the information from the imaging optical system.

By the way, in the above-described embodiment, use was made of the imaging sight as in the imaging conditions. In case, however, the imaging means is equipped with a mechanism for correcting astigmatism, such astigmatism correcting information can also be utilized for correcting the distortional aberration. In this case, the above-mentioned correction function is no longer concentric. In other words, when the correction function is plotted on the co-ordinate of each image data as (r, θ), the imaging sight d becomes different depending on the angular direction, which can be represented as the function d(θ) of θ. Accordingly, by substituting this d(θ) for the above-mentioned function F(r, d), the correction function can be represented as r'=F(r, d(θ)).

Also, generation of the distortional aberration depends on the light wavelength, i.e. color (chromatic aberration of magnification), which is a cause for the color bleeding in the image. Therefore, when the above-mentioned image data is a color image, the image data are decomposed into the original color images of red (R), green (G), blue (B), and so forth, and the distortional aberration may be corrected for each of the color image data as decomposed. In this case, the coefficient of the abovementioned correction function includes a wavelength λ as a variable, which can be represented by A(d, λ), B(d, λ), C(d, λ), and D(d, λ), hence the correction function can be represented as r'=F(r, d, λ).

Incidentally, the present invention is not limited only to the correction of position of each part of the image (i.e. correction of image distortion), as in the above-described embodiment, but it can also correct darkness of each and every part of the image (i.e. correction of brightness distribution). In some cases, the eye fundus image falls short of an amount of light on its periphery owing to an influence caused by vignetting, etc. in the imaging optical system. Since this shortage of light differs from one imaging condition to another, if and when the correction function is produced for every imaging condition to correct the brightness distribution on the image in such a manner that the brightness increases towards the peripheral part of the image, there will be obtained an image having accurate brightness distribution. More concretely, the corrective darkness t'(r) with respect to darkness t at the position of r is represented, for example, by the following function:

$$F(t, d)=A_1(d)+B_1(d)t+C_1(d)t^2+D_1(d)t_3.$$

Figure 3:
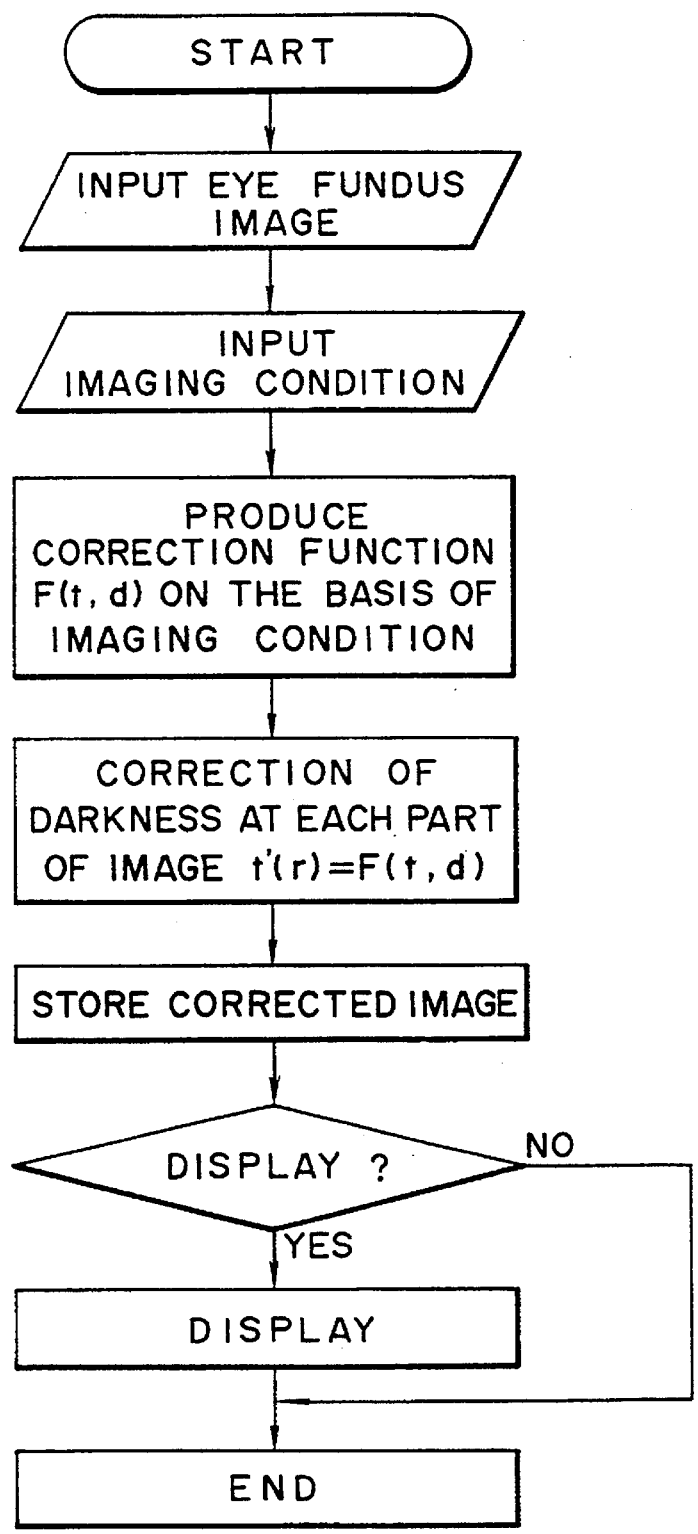
FIG. 3 is a flow chart for carrying out correction of darkness of each and every part of an image.

A flow chart of a series of these processes are shown in FIG. 3. It goes without saying that the correction of darkness of each part of the image can be effected along with the position correction of each part of the image as mentioned above.

In the above-described embodiment, use was made of the sight d as the information to represent the state of the imaging optical system, and it is also feasible to use the imaging magnification β. That is to say, the detecting means 8 in the above-described embodiment is employed as the one having its imaging magnification β, and the distortional aberration is corrected in utilizing its magnification information. The coefficient of the abovementioned correction function F at this instant is the function of the imaging magnification β, hence A(β), B(β), C(β), and D(β), whereby the correction function can be represented as r'=F(r, β) or t'=F(t, β). As a matter of course, it is feasible that, taking the entire parameters into consideration, the correction function can be formulated as: r'=F(r, d(θ), λ, β) or t'=F(t, d(θ), λ, λ).

Further, the imaging conditions can be expressed as r'=F(r,α) by use of a relative disposition condition of a fixed viewing optical system with respect to the imaging optical system, i.e., an angle α formed by the viewing axis of an eye to be photographed and the optical axis of the imaging optical system.

More concertely, there may be employed two modes of correction: the one is to set the fixed viewing optical system (inclusive of a fixed viewing light source) at a reference position, and to rotate the imaging optical system at a certain angle with the position of the pupil of an eye to be inspected being made as the center of its rotation (i.e. this angle corresponding to tilting or panning of the eye fundus camera); and the other is to set the imaging optical system at a reference position, and to rotate the fixed viewing optical system at a certain angle with the position of the pupil of an eye to be inspected being made as the substantial center of its rotation (i.e. this angle being obtainable from the height position, with respect to the optical axis, of the imaging optical system of an external fixed viewing lamp or an internal fixed viewing lamp).

Figure 4:
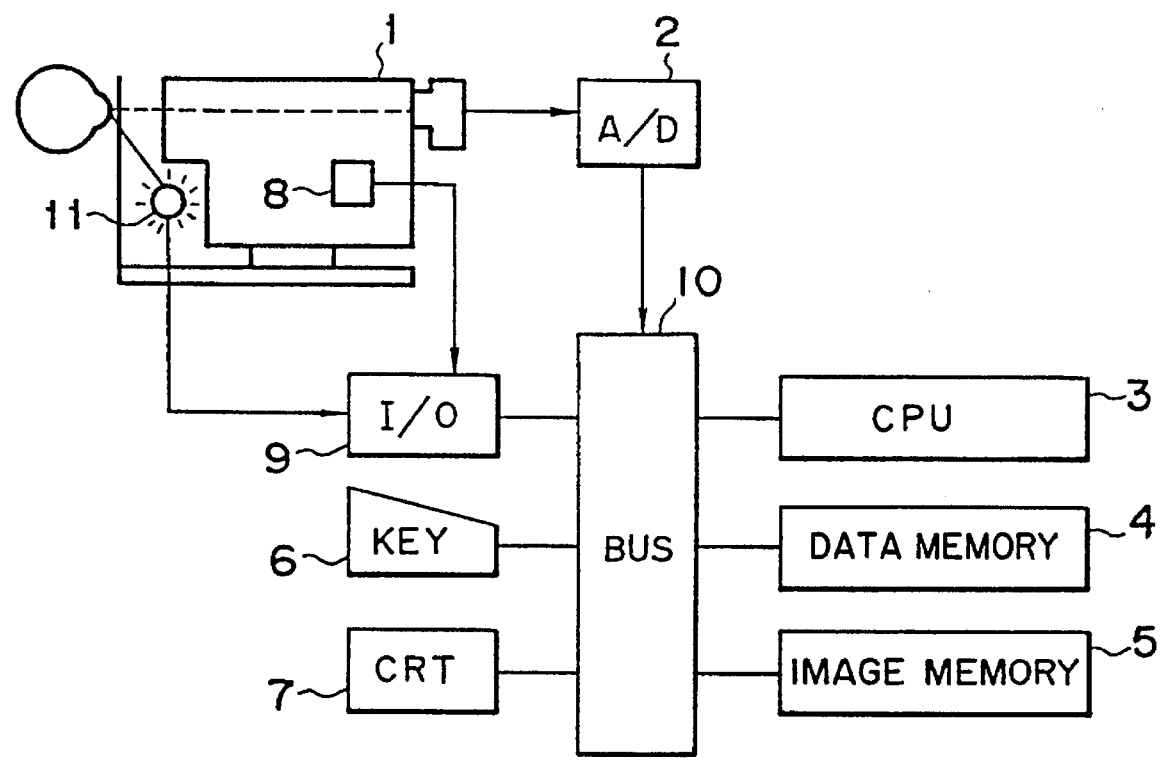
FIG. 4 is a block diagram showing a construction of the image processing apparatus according to another embodiment of the present invention.

FIG. 4 illustrates a case where the external fixed viewing lamp 11 is used for the fixed viewing optical system. In this figure, those reference numerals which are identical with those in FIG. 1 designate the same constituent parts. With use of this apparatus, when a plurality of eye fundus images taken at a plurality of different imaging angles, for one and the same eye to be inspected, are corrected by the abovementioned method, and then 1 such eye fundus images are joined together, there can be performed the accurate inspection of the eye fundus over a wide angular range.

In the following, explanations will be provided of to the correction of the eye fundus image, when there occurs a change in the relative disposition of the fixed viewing optical system with respect to the imaging optical system. That is, to say, on the one hand, the distortional aberration of the eye to be inspected itself and that of the imaging optical system itself are independent of each other, and the center of correction of the distortional aberration of the imaging optical system itself is constantly at the center of the image; and, on the other hand, the center of correction of the distortional aberration in the eye to be inspected itself takes a position conjugated with the fixed viewing point in the image. As a consequence of this, there may be carried out two corrective actions, i.e., the one with the center of the image being made as the center of correction, and the other with the conjugated position and the fixed viewing point in the image being made as the center of correction; or there may be carried out a single corrective action which is a combination of the above-mentioned two corrective actions.

Incidentally, it goes without saying that the imaging conditions may not only be the abovementioned angle α, but also be a combination of this angle α and at least one of the sight d, the magnification β, and the wavelength λ.

Further, as the imaging condition, there may also be used, besides the sight d, the magnification β and the angle α, a working distance l between the eye to be inspected and the imaging optical system.

It should be noted that the image which can be processed by the apparatus of the present invention is not limited to the eye fundus image as described in the foregoing embodiments, but it can be widely adopted in processing images in general, not to say of various medical images such as, for example, images taken by an endoscopic camera, gastroscopic camera, and so forth.

Although, in the foregoing, the present invention has been described in specific details with reference to its preferred embodiments, it should be understood that the invention is not limited to these embodiments alone, but any changes and modifications may be made by those persons skilled in the art, without departing from the spirit and scope of the invention as recited in the appended claims.

What is claimed is:

1. An opthalmological image processing apparatus comprising:

an eye fundus image phototaking system for phototaking an eye fundus image through a phototaking optical system, wherein said phototaking optical system has a focusing function to change a diopter of said phototaking optical system so that a focusing operation can be performed on an eye fundus of each of eyes to be examined having various refracting powers and wherein said phototaking optical system generates different distortions according to the diopter changed by said focusing function for an image to be phototaken when focusing by said focusing operation is completed;

a diopter detector for detecting diopter data of said phototaking optical system;

a converter for converting data of the eye fundus image obtained by said eye fundus image phototaking system into digital data;

a first memory for storing said eye fundus image data converted to digital data by said converter;

a second memory for storing a correction scheme for correcting images, said correcting scheme being performed with varying correction processes in accordance with the diopter data of said phototaking optical system; and an image processing portion for correcting distortion of said eye fundus image data stored by said first memory according to the correction scheme stored by said second memory and the diopter data detected by said diopter detector, wherein the diopter data detected by said diopter detector is converted into a form which said image processing portion can read and which can be sent to said image processing portion.

2. An apparatus according to claim 1, wherein said phototaking optical system further has a magnifying function for changing a phototaking magnification and said image processing portion also corrects distortion of said eye fundus image data according to said phototaking magnification.

3. An ophthalmological image processing apparatus comprising:

an eye fundus image phototaking system for phototaking an eye fundus image through a phototaking optical system, wherein said phototaking optical system has a focusing function to change a diopter of said optical system so that a focusing operation can be performed on an eye fundus of each of eyes to be examined having various refracting powers and wherein said phototaking optical system generates different distortions according to the diopter changed by said focusing function for an image to be phototaken when focusing by said focusing operation is completed;

a diopter detector for detecting a diopter of said phototaking optical system;

a converter for converting data of the eye fundus image obtained by said eye fundus image phototaking system into digital data;

a memory for storing said eye fundus image data converted to digital data by said converter; and an image processing portion for correcting distortion of said eye fundus image data stored by said memory according to the diopter detected by said diopter detector, said image processing portion performing different correction of distortion for each color in said eye fundus image data.

4. An ophthalmological image processing method comprising the steps of:

obtaining eye fundus image data through a phototaking optical system, wherein said phototaking optical system has a focusing function to change a diopter of said optical system so that a focusing operation can be performed on an eye fundus of each of eyes to be examined having various refracting powers and wherein said phototaking optical system generates different distortion according to the diopter changed by said focusing function for an image to be phototaken when focusing by said focusing operation is completed;

obtaining diopter data of the phototaking optical system when said eye fundus image data are obtained;

converting the obtained eye fundus image data into digital data;

storing said eye fundus image data converted to said digital data;

storing a correction scheme for correcting distortion of images, said correction scheme being performed with varying correction processes in accordance with the diopter data of said phototaking optical system; and image-processing said stored eye fundus image data, wherein distortion of said eye fundus image data is corrected according to the stored correction scheme and said obtained diopter data by said image processing step with an image processor, wherein the diopter data obtained is converted into a form which the image processor can read and which can be sent to the image processor.

5. An ophthalmological image processing apparatus comprising:

an eye fundus image phototaking system for phototaking an eye fundus image through a phototaking optical system, wherein said phototaking optical system has a focusing function to change a diopter of said optical system so that a focusing operation can be performed on an eye fundus of each of eyes to be examined having various refracting powers and wherein said phototaking optical system generates different shadings according to the diopter changed by said focusing function for an image to be phototaken when focusing by said focusing operation is completed;

a diopter detector for detecting a diopter data of said phototaking optical system;

a converter for converting data of the eye fundus image obtained by said eye fundus image phototaking system into digital data;

a first memory for storing said eye fundus image data converted to digital data by said converter;

a second memory for storing a correction scheme for correcting distortion of image, said correction scheme being performed with varying correcting processes in accordance with the diopter data of said phototaking optical system; and an image processing portion for correcting shading of said eye fundus image data stored by said first memory according the correction scheme stored by said second memory and the diopter data detected by said diopter detector, wherein the diopter data detected by said diopter detector is converted into a form which said image processing portion can read and which can be sent to said image processing portion.

6. An apparatus according to claim 5, wherein said phototaking optical system further has a magnifying function for changing a phototaking magnification thereof and said image processing portion also corrects shading of eye fundus image data according to said phototaking magnification.

7. An ophthalmological image processing method comprising the steps of:

obtaining eye fundus image data through a phototaking optical system, wherein said phototaking optical system has a focusing function to change a diopter of said optical system so that a focusing operation can be performed on an eye fundus of each of eyes to be examined having various refracting powers and wherein said phototaking optical system generates different shadings according to the diopter changed by said focusing function for an image to be phototaken when focusing by said focusing operation is completed;

obtaining diopter data of said phototaking optical system when said eye fundus image data are obtained;

converting the obtained eye fundus image data into digital data;

storing the eye fundus image data converted to digital data;

storing a correction scheme for correcting shading of images, said correction scheme being performed with varying correction processes in accordance with the diopter data of the phototaking optical system; and image-processing the stored eye fundus image data, wherein shading of eye fundus image data is corrected according to the stored correction scheme and said obtained diopter data by said image processing operation with an image processor, wherein the obtained diopter data is converted into a form which the image processor can read and which can be sent to said image processor.

8. An ophthalmological image processing apparatus comprising:

an eye fundus image phototaking system for phototaking an eye fundus image through a phototaking optical system, wherein said phototaking optical system has a magnification varying function to change a magnification of the eye fundus image phototaken thereby and wherein said phototaking optical system generates different distortions according to the magnification changed by said magnification varying function for an image to be phototaken;

a magnification detector for detecting phototaking magnification data of said phototaking optical system;

a convertor for converting data of the eye fundus image obtained by said eye fundus image phototaking system into digital data;

an image memory for storing said eye fundus image data converted to digital data by said converter;

a data memory for storing a correction scheme for correcting distortion of images, said correction scheme being performed with varying correcting processes in accordance with the phototaking magnification data of said phototaking optical system; and an image processing portion for correcting distortion of the eye fundus image data stored by said image memory according to the correction scheme stored by said data memory and the phototaking magnification data detected by said magnification detector, wherein the phototaking magnification data detected by said magnification detector is converted into a form which said image processing portion can read and which can be sent to said image processing portion.

9. An ophthalmological image processing apparatus comprising:

an eye fundus image phototaking system for phototaking an eye fundus image through a phototaking optical system, wherein said phototaking optical system has a magnification varying function to change a magnification of the eye fundus image phototaken thereby and wherein said phototaking optical system generates different distortions according to the magnification changed by said magnification varying function for an image to be phototaken;

a magnification detector for detecting phototaking magnification data of said phototaking optical system;

a converter for converting data of the eye fundus image obtained by said eye fundus image phototaking system into digital data;

an image memory for storing the eye fundus image data converted to digital data by said converter;

a data memory for storing a correction scheme for correcting shading of images, said correction scheme being performed with varying correction processes in accordance with the phototaking magnification data of said phototaking optical system; and an image processing portion for correcting shading of the eye fundus image data stored by said image memory according to the correction scheme stored by said data memory and the phototaking magnification data detected by said magnification detector, wherein the phototaking magnification data detected by said magnification detector is converted into a form which said image processing portion can read and which can be sent to said image processing portion.

* * * * *